United States Patent [19]

Becking

[11] Patent Number: 5,525,207
[45] Date of Patent: Jun. 11, 1996

[54] POLYALKYLENE GLYCOL BIS-PHENYL-A-SULFOPROPYL DIETHER COMPOUND AND THEIR SALTS, AND PROCESS FOR THEIR USE

[75] Inventor: Donald H. Becking, Southington, Conn.

[73] Assignee: Mac Dermid, Incorporated, Waterbury, Conn.

[21] Appl. No.: 509,027

[22] Filed: Jul. 28, 1995

Related U.S. Application Data

[63] Continuation-in-part of Ser. No. 324,241, Oct. 14, 1994, abandoned.
[51] Int. Cl.[6] .............................. C25D 3/22; C25D 3/32
[52] U.S. Cl. ..................... 205/244; 205/254; 205/238; 205/302; 205/311; 205/313
[58] Field of Search ................................. 205/244, 253, 205/254, 302, 313, 238, 311

[56] References Cited

U.S. PATENT DOCUMENTS

| | | | |
|---|---|---|---|
| 4,592,809 | 6/1986 | Feng et al. | 204/44.2 |
| 4,820,388 | 4/1989 | Kurze et al. | 204/44.2 |

Primary Examiner—John Niebling
Assistant Examiner—Kishor Mayekar
Attorney, Agent, or Firm—John L. Cordani

[57] ABSTRACT

The present invention relates to a novel composition of matter, and a process for its use as an electroplating additive for enhancing the performance of a plating bath. Polyalkylene glycol bis-phenyl-A-Sulfopropyl diether compounds and their salts are proposed and their usefulness as plating bath additives is disclosed.

4 Claims, No Drawings

POLYALKYLENE GLYCOL BIS-PHENYL-A-SULFOPROPYL DIETHER COMPOUND AND THEIR SALTS, AND PROCESS FOR THEIR USE

This application is a continuation-in-part of U.S. Patent application Ser. No. 08/324,241 filed Oct. 14, 1994 now abandoned.

FIELD OF THE INVENTION

The present invention relates to a novel composition of matter, and a process for its use as an electroplating additive for enhancing the performance of a plating bath, particularly acid zinc, zinc alloy, tin, or tin alloy plating baths.

BACKGROUND OF THE INVENTION

The invention relates to novel Polyalkylene glycol bisphenyl-A-sulfopropyl diethern and salts thereof. Also disclosed is a process for their use as additives to electroplating baths, particularly acid zinc electroplating baths, for the purpose of enhancing the appearance, integrity, and performance of the electroplated deposits.

U.S. Pat. No. 4,820,388 (Kurze), incorporated herein in its entirety by reference, reveals novel compositions of matter comprising polyalkylene glycol naphthyl-3-sulfopropyl diethers and their use as surfactants in electroplating baths. These compounds and the process revealed, have worked well, however, these compounds have a significant drawback, a relatively low cloud point in aqueous solutions when reasonable concentrations of the compounds are utilized, i.e. from 1 to 2 g/L of the compound. Higher cloud points are only obtainable with these compounds in aqueous solution when very high concentrations are utilized (from 3 to 10 g/L).

The cloud point of a compound is the temperature at which the compound begins to precipitate out of solution at a given concentration and solvent mixture. Thus, it has been discovered that the compounds of Kurze possess a relatively low cloud point, particularly under the conditions that they are used in electroplating baths as performance additives.

Electroplating baths, by their very nature, tend to rise in temperature during use because of the current necessary for operation and the solution's electrical resistance. Therefore, as an electroplating bath is used and it heats up, compounds such as the Kurze compounds which have low cloud points at the concentrations effectively utilized in electroplating solutions, will begin to precipitate from solution. This precipitation of these compounds and the other additives which they solubilize, then causes poor bath performance and inconsistency in the plating results. Thus, the performance of electroplating baths can be measurably improved by utilizing plating additives with higher cloud points.

It has now been found that the compounds of the present invention provide all of the advantages of the prior art compounds along with an additional advantage of processing a higher cloud point at any given concentration in aqueous solution, particularly when utilized as electroplating bath performance additives.

SUMMARY OF THE INVENTION

The polyalkylene glycol bisphenyl-A-sulfopropyl diethers of the present invention have significant advantages over exiting compounds in several areas. The compounds of this invention possess relatively high cloud points in aqueous solutions at any given concentration. Because of this, the same or better results can be achieved at lower concentrations when utilizing these compounds as opposed to the compounds taught in Kurze. The lower concentrations then translate into lower costs and more environmentally sound products and processes.

In addition, because the compounds of this invention tend to remain in aqueous solution at higher temperatures and therefore tend to solubilize other additives better, they produce superior more consistent results. This is particularly true in the field of metal plating where the compounds of this invention are advantageously utilized. In metal plating baths, these compounds serve a dual purpose. First, they themselves act as performance additives and thereby brighten and level the deposit. Secondly, they serve to solubilize other performance additives into the solution of the metal plating bath. The Kurze compounds also perform similar functions in plating but the Kurze compounds require relatively higher concentrations to achieve the same results and cloud point level as the compounds of the present invention.

In fact, at high levels of concentration, the compounds of this invention produce plating performance which far exceeds those obtainable by the Kurze compounds at any concentration. Finally, since the compounds of this invention tend to remain in solution more consistently, and to solubilize other additives more effectively, they produce more consistent plating results. In conclusion, therefore, diethern of the present invention out-perform previously known compounds in many areas of application.

DETAILED DESCRIPTION OF THE INVENTION

The polyalkylene glycol bisphenyl-A-sulfopropyl diethers of this invention have the general formula:

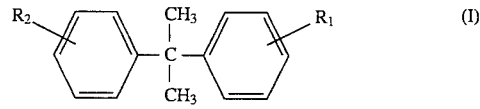 (I)

Wherein, $R_1$ represents any reaction point on its ring, and is selected from the group consisting of Na—SO$_3$—C$_3$H$_6$—(—O—CH$_2$—CH$_2$)$_x$—O, Na—SO$_3$—C$_3$H$_6$—(—O—CH$_2$—CH$_2$—CH$_2$)$_x$—O, Na—SO$_3$—C$_3$H$_6$—([OCH$_2$ CH$_2$]$_A$ [O— CH$_2$—CH$_2$ CH$_2$]$_B$)$_x$—O, H—(OCH$_2$CH$_2$—CH2)$_x$—O, H—([O—CH$_2$—CH$_2$—CH$_2$]$_A$ [O—CH$_2$ CH$_2$]$_B$)$_x$—O and H—(OCH$_2$—CH$_2$)$_x$—O and wherein $R_2$ represents any reaction point on its ring, and is selected from the group consisting of Na—SO$_3$—C$_3$H$_6$—(—O—CH$_2$—CH$_2$)$_x$—O, Na—SO$_3$—C$_3$H$_6$—(—O—CH$_2$—CH$_2$—CH$_2$)$_x$—O,Na—SO$_3$—C$_3$H$_6$ —([OCH$_2$ — CH$_2$]$_A$ [O—CH$_2$—CH$_2$—CH$_2$]$_B$)$_x$—O, H— (OCH$_2$CH$_2$—CH$_2$)$_x$—O, H—([O—CH$_2$—CH$_2$ CH$_2$]$_A$ [O—CH$_2$—CH$_2$]$_B$)$_x$—O and H—(—OCH$_2$—CH$_2$)$_x$—O, and wherein x=5 to 80 and $_B$=0 to 80, $_A$=0 to 80 provided however, that at least one $R_1$ or $R_2$ has Na—SO$_3$—C$_3$H$_6$ functionality.

Compounds of Formula I are prepared by ethyoxylating and/or propoxylating a corresponding bis-phenyl A with ethylene oxide and/or propylene oxide in a known manner and then further reacting the product of the former reaction with propane- 1,3-Sultone in the presence of alkali hydroxides, earth alkali hydroxides or quaternary ammonium hydroxides. The reaction with propane sultone is carried out at temperatures in the range of 0° to 100° C. depending upon the chain length from the alkoxy group and the desired reaction speed.

The preferred compounds of the invention for use as electroplating additives are the following:

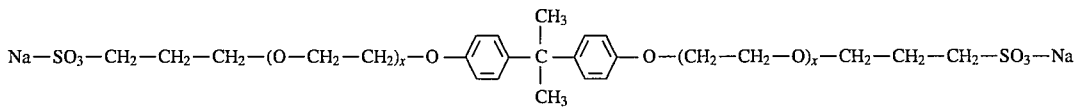

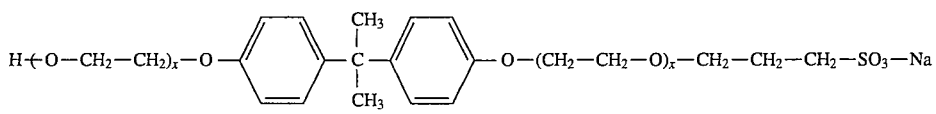

wherein, –x=15

The compounds of the present invention, particularly the most preferred compounds, are advantageously employed as electroplating bath additives. These compounds provide several important functions in plating baths. Firstly, they tend to solubilized other additives into the solution of the bath. Secondly, they act as deposit brighteners and levelers themselves. In their capacity as plating additives, it is essential that these compounds remain in solution under a wide variety of conditions. One of the most important characteristics of the compounds of this invention is their unusually high cloud point at any given concentration under electroplating conditions. This unusually high cloud point gives optimum performance and consistency.

Example I

The production of disodium salt of polyethylene glycol-2 (-bis-phenyl A) - (3-sulfopropyl) diether:

To 1 mole of bis-phenyl-A-(ethoxylate)$_n$ (n–30 to 40) there are added 2.02 moles of sodium hydroxide with stirring for 30 minutes. Thereafter, 2 moles of molten propane -1,3 sultone are added and the temperature is maintained from 40°–50° C. for 4 to 5 hours. The reaction product is a light brown solid (n=30) with the following properties:

| Content of compound | 75 to 85% | According to two phase |
| --- | --- | --- |
| Water | 7 to 12% | Karl Fischer titration. |
| pH | 9 to 12 | (10% in water) |
| Water Solubility | Good Solubility | |

Example II

A zinc electroplating bath was formulated with the following composition:

| | |
| --- | --- |
| Zinc Chloride | 38 g/L |
| Potassium Chloride | 224 g/L |
| Boric Acid | 40 g/L |
| Ammonium benzoate | 0.5 g/L |
| Polyethylene glycol-2-(bis-phenyl A)-(3-Sulfopropyl) diether (Example I) | 2 g/L |
| Glycine | 0.5 g/L |
| Glycerine Ethoxylate | 1¼ g/L |
| Ethoxylated B-Napthol | 0.2 g/L |

Hull cells were run utilizing the above indicated electroplating composition. The Hull Cell panels were very bright and smooth. The bath was allowed to heat as plating continued. The zinc plate which was produced, remained unaffected by the heat and was continuously bright and smooth. The cloud point of the electroplating solution was determined to be 175° F. and remained essentially constant over time.

Example III

A tin electroplating bath was formulated with the following composition:

| | |
| --- | --- |
| Tin Sulfate | 1.5 oz as tin metal |
| Sulfuric Acid | 12.5 oz |
| Polyethylene glycol-2-(bis-phenyl-A)-(3-Sulfopropyl) diether (Example I) | 1 g/L. |
| Synfac 8216 (Ethoxylated Styrenated Phenol) | 2 g/L |
| Synfac Tea (Ethoxylated B Triethanolamine) | 1 g/L |

Hull cells were run utilizing the above indicated electroplating composition. The Hull Cell panels were white, bright and smooth. Good coverage was obtained on the back of the panel and no burning was found on the front plating at 2 amps for 5 minutes. The tin plate was unaffected by heat and was continuously smooth and bright. The cloud point of the solution was determined to be approximately 175° F. and remained essentially constant over time.

Example IV

A tin alloy electroplating bath was formulated with the following composition:

| | |
| --- | --- |
| Tin Fluoborate | 10 g/L |
| Lead Fluoborate | 4.5 g/L |
| Fluoboric Acid | 120 g/L |
| Boric Acid | 15 g/L |
| Polyethylene glycol-2-(bis-phenyl A)-(3-Sulfopropyl) diether (Example I) | 1 g/L |
| Catechol | 4 g/L |
| 2,4 Dichlorobenzaldehyde | 0.2 g/L |

Hull cells were run utilizing the above indicated electroplating composition. The Hull Cell panels were white, bright and smooth. Good coverage was obtained on the back of the panel and no burning was found on the front plating at 2 amps for 5 minutes. The tin alloy plate was unaffected by heat and was continuously smooth and bright. The cloud point of the solution was determined to be approximately 175° F. and remained essentially constant over time.

I claim:

1. An acidic electroplating bath comprising at least one polyalkylene glycol bisphenyl-A-sulfopropyl diether of the formula:

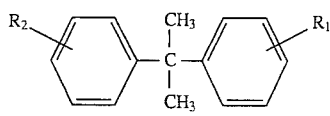 (I)

wherein any reaction point on its ring, selected from the group consisting of Na—$SO_3$—$C_3H_6$—(—O—$CH_2$—$CH_2$)$_x$—O, Na—$SO_3$—$C_3H_6$—(—O—$CH_2$—$CH_2$—$CH_2$)$_x$—O, Na—$SO_3$—$C_3H_6$—([$OCH_2$ $CH_2$]$_A$ [O—$CH_2$—$CH_2$—$CH_2$]$_B$)$_x$—O, H—($OCH_2CH_2$—$CH2$)$_x$—O, H—([O—$CH_2$—$CH_2$—$CH_2$]$_A$ [O—$CH_2$—$CH_2$]$_B$)$_x$—O and H—($OCH_2$—$CH_2$)$_x$—O; $R_2$ represents any reaction point on its ring and is selected from the group consisting of Na—$SO_3$—$C_3H_6$—(—O—$CH_2$—$CH_2$)$_x$—O, Na—$SO_3$—$C_3H_6$—(—O—$CH_2$—$CH_2$—$CH_2$)$_x$—O, Na—$SO_3$—$C_3H_6$—([$OCH_2$—$CH_2$]$_A$ [O—$CH_2$—$CH_2$—$CH_2$]$_B$)$_x$—O, H—($OCH_2CH_2$—$CH_2$)$_x$—O, H—([O—$CH_2$—$CH_2$—$CH_2$]$_A$ [O—$CH_2$—$CH_2$]$_B$)$_x$—O and H—(—$OCH_2$—$CH_2$)$_x$—O; x=5 to 80; B=0 to 80; and A=0 to 80 provided however, that at least one the $R_1$ or $R_2$ has Na—$SO_3$—$C_3H_6$ functionality.

2. An electroplating bath, according to claim 1 for depositing zinc or a zinc alloy.

3. An electroplating bath according to claim 1 for depositing tin or tin alloys.

4. A method for electroplating an article, said method comprising contacting the article to be plated with an acidic electroplating bath comprising a compound of the following formula:

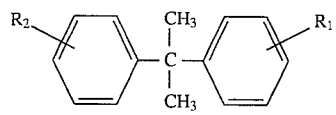

wherein $R_1$ represents any reaction point on its ring, selected from the group consisting of Na—$SO_3$—$C_3H_6$—(—O—$CH_2$—$CH_2$)$_x$—O, Na—$SO_3$—$C_3H_6$—(—O—$CH_2$—$CH_2$—$CH_2$)$_x$—O, Na—$SO_3$—$C_3H_6$—([$OCH_2$ $CH_2$]$_A$ [O—$CH_2$—$CH_2$—$CH_2$]$_B$)$_x$—O, H—($OCH_2CH_2$—$CH_2$)$_x$—O, H—([O—$CH_2$—$CH_2$—$CH_2$]$_A$ [O—$CH_2$—$CH_2$]$_B$)$_x$—O and H—(O—$CH_2$—$CH_2$)$_x$—O; $R_2$ represents any reaction point on its ring and is selected from the group consisting of Na—$SO_3$—$C_3H_6$—(—O—$CH_2$—$CH_2$)$_x$—O, Na—$SO_3$—$C_3H_6$—(—O—$CH_2$—$CH_2$)$_x$—O, Na—$SO_3$—$C_3H_6$—([$OCH_2$—$CH_2$]$_A$ [O—$CH_2$—$CH_2$—$CH_2$]$_B$)$_x$—O, H—($OCH_2CH_2$—$CH_2$)$_x$—O, H—([O—$CH_2$—$CH_2$—$CH_2$]$_A$ [O—$CH_2$—$CH_2$]$_B$)$_x$—O and H—(—$OCH_2$—$CH_2$)—O; x=5 to 80; B=0 to 80; and A=0 to 80 provided however, that at least one the $R_1$ or $R_2$ has Na—$SO_3$—$C_3H_6$ functionality.

* * * * *

UNITED STATES PATENT AND TRADEMARK OFFICE
CERTIFICATE OF CORRECTION

PATENT NO. : 5,525,207

DATED : June 11, 1996

INVENTOR(S) : Donald H. Becking

It is certified that error appears in the above-identified patent and that said Letters Patent is hereby corrected as shown below:

Column 5, line 6, add --$R_1$ represents-- after "wherein" and before "any".
Column 5, line 6, after "ring" delete "," and insert --and is-- before "selected".

Column 6, line 8, add --and is-- after "ring" and before "selected".

Signed and Sealed this

Nineteenth Day of November, 1996

Attest:

BRUCE LEHMAN

Attesting Officer

Commissioner of Patents and Trademarks